US012629684B2

(12) United States Patent
Shkolnikov et al.

(10) Patent No.: US 12,629,684 B2
(45) Date of Patent: May 19, 2026

(54) NUCLEIC ACID AMPLIFICATION

(71) Applicant: HEWLETT-PACKARD DEVELOPMENT COMPANY, L.P., Spring, TX (US)

(72) Inventors: Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 842 days.

(21) Appl. No.: 17/911,838

(22) PCT Filed: Apr. 29, 2020

(86) PCT No.: PCT/US2020/030445
§ 371 (c)(1),
(2) Date: Sep. 15, 2022

(87) PCT Pub. No.: WO2021/221629
PCT Pub. Date: Nov. 4, 2021

(65) Prior Publication Data
US 2023/0173497 A1        Jun. 8, 2023

(51) Int. Cl.
*C12Q 1/68* (2018.01)
*B01L 3/00* (2006.01)
(Continued)

(52) U.S. Cl.
CPC ........... *B01L 7/52* (2013.01); *B01L 3/502715* (2013.01); *B01L 3/502761* (2013.01);
(Continued)

(58) Field of Classification Search
None
See application file for complete search history.

(56) References Cited

U.S. PATENT DOCUMENTS 5,849,208 A      12/1998  Hayes et al.
9,388,465 B2 *   7/2016   Hindson ............ G01N 33/5436
(Continued)

FOREIGN PATENT DOCUMENTS

CN      109988709 A      7/2019
EP       0572057 A1     12/1993
(Continued)

OTHER PUBLICATIONS

Puddu, M., et al. "Magnetically recoverable, thermostable, hydrophobic DNA/silica encapsulates and their application as invisible oil tags." ACS Nano, Feb. 25, 2014, vol. 8, No. 3, pp. 2677-2685.
(Continued)

*Primary Examiner* — Aaron A Priest
(74) *Attorney, Agent, or Firm* — Foley & Lardner LLP

(57) ABSTRACT

Examples relate to techniques for performing a nucleic acid amplification reaction. The method includes generating a nucleic acid solution comprising a plurality of nucleic acid molecules, and combining the nucleic acid solution with a plurality of chamber particles. Each chamber particle includes a chamber for receiving the nucleic acid solution, wherein the chamber receives, at most, one of the plurality of nucleic acid molecules. Each chamber particle also includes reagents for causing a polymerase chain reaction within the chamber. The method further includes inducing nucleic acid amplification to generate an amplified nucleic acid, and performing a detection process to detect the presence of the amplified nucleic acid within the chamber.

4 Claims, 11 Drawing Sheets

(51) Int. Cl.
  *B01L 7/00* (2006.01)
  *C12Q 1/686* (2018.01)

(52) U.S. Cl.
  CPC ...... *C12Q 1/686* (2013.01); *B01L 2300/0896*
    (2013.01); *B01L 2400/043* (2013.01); *B01L*
    *2400/0487* (2013.01)

(56) References Cited

U.S. PATENT DOCUMENTS

| | | | |
|---|---|---|---|
| 11,040,349 B2* | 6/2021 | Kawashima | .......... B01L 3/0268 |
| 2005/0202429 A1 | 9/2005 | Trau et al. | |
| 2013/0005591 A1 | 1/2013 | Cai | |
| 2013/0225421 A1 | 8/2013 | Li et al. | |
| 2016/0107159 A1* | 4/2016 | Gong | ....................... B01L 3/567 |
| | | | 435/6.12 |
| 2019/0331677 A1 | 10/2019 | Steinmetzer et al. | |
| 2019/0352591 A1* | 11/2019 | Steemers | .......... A61K 47/6937 |

| | | | |
|---|---|---|---|
| 2019/0381497 A1* | 12/2019 | Di Carlo | .............. C12Q 1/6804 |
| 2020/0131502 A1* | 4/2020 | Norberg | ................... B01J 13/22 |
| 2020/0263244 A1* | 8/2020 | Bashir | ................. C12Q 1/6806 |

FOREIGN PATENT DOCUMENTS

| | | |
|---|---|---|
| WO | 2018/122162 A1 | 7/2018 |
| WO | 2019/129580 A1 | 7/2019 |
| WO | 2020/037214 A1 | 2/2020 |

OTHER PUBLICATIONS

Suvorova, A.O. et al., "Development of a microchip analytical system with PCR reagents lyophilized into aluminum microchips and modified by the plasma enhanced chemical vapor deposition," Analytics and Control, Apr. 19, 2015, vol. 19, No. 4, pp. 331-339. (English Abstract).

Tian, Q., et al., "An integrated temporary negative pressure assisted microfluidic chip for DNA isolation and digital PCR detection," RSC Advances, Sep. 14, 2015, vol. 5, pp. 81889-81896.

* cited by examiner

500

600

810

806

804

802

812

806

804

802

100          100

806

802

1000
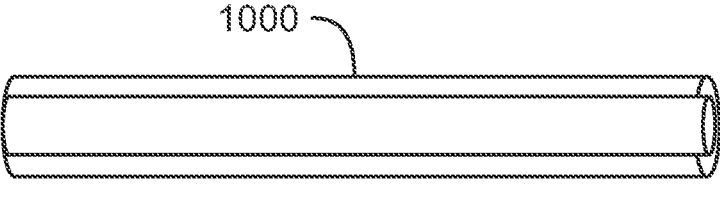
FIG. 10A
1000                    1002
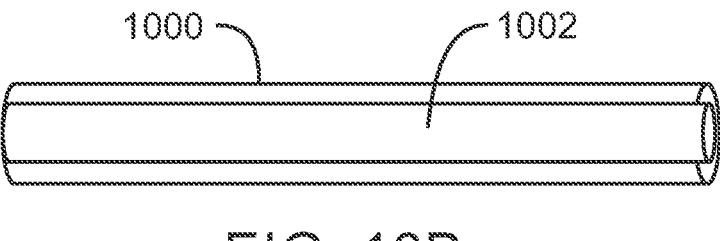
FIG. 10B
1000                    1004
FIG. 10C
1000          1004          100
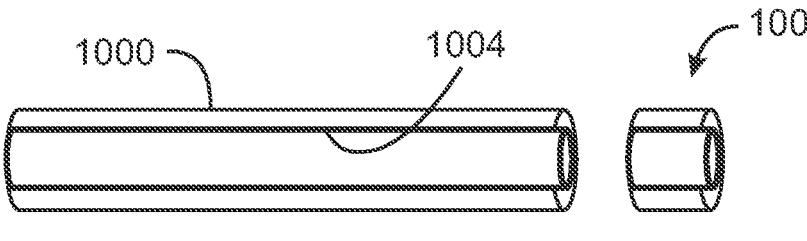
FIG. 10D

NUCLEIC ACID AMPLIFICATION

CROSS-REFERENCE TO RELATED APPLICATIONS

This application is a U.S. National Stage Application under 35 U.S.C. § 371 of International Application No. PCT/US2020/030445, filed Apr. 29, 2020, which is incorporated by reference herein.

BACKGROUND

Nucleic acid testing is widely used for disease diagnostics, and its importance in disease diagnostics market is increasing, especially in diagnosis of infectious diseases. Polymerase chain reaction (PCR) is a nucleic acid testing technique used in molecular biology to make multiple copies of a specific deoxyribonucleic acid (DNA) segment. Using PCR, a copy of a DNA sequence can be exponentially amplified to generate many more copies of that particular DNA segment. Digital droplet PCR is a specific type of PCR technique that can be used to quantify with high precision the number of copies of a nucleic acid sequence in a sample. Such quantitative analysis may be useful for determining the concentration of a target analyte within a sample.

DESCRIPTION OF THE DRAWINGS

Certain examples are described in the following detailed description and in reference to the drawings, in which:

FIGS. 10A through 10D illustrate another example technique for fabricating chamber particles.

DETAILED DESCRIPTION

Figure 1A:
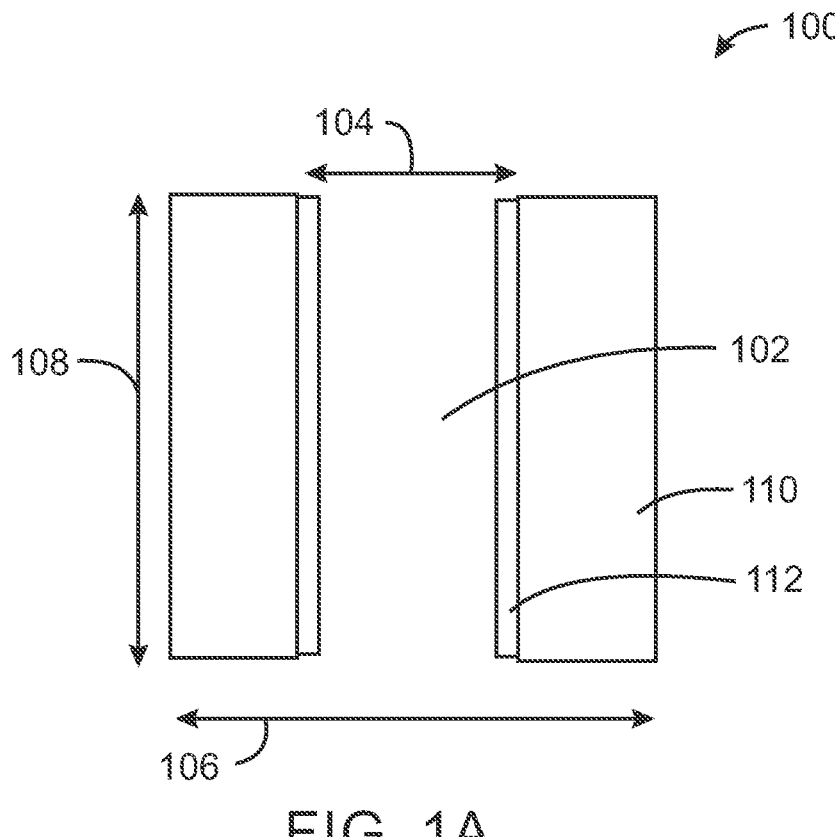
FIG. 1A is a cross sectional view of an example chamber particle.

This present disclosure relates to nucleic acid amplification techniques such as digital polymerase chain reaction (PCR). Digital PCR is a quantitative technique used to measure the quantity of a target DNA sequence in a DNA sample. In digital PCR, the DNA sample is highly diluted and singulated into individual droplets so that some of them do not receive a single molecule of the target DNA. After running PCRs in parallel on each droplet, the target DNA concentration can be calculated using the proportion of negative to positive outcomes. In digital droplet PCR, the sample to be tested is split, diluted, and singulated into droplets such that each droplet contains no more than a single copy of the nucleic acid material. The individual droplets are provided with various reagents that cause nucleic acid amplification. This method requires the step of droplet generation, often performed by a stand-alone instrument, which deposits a large number of separate droplets within separate wells of a microwell plate such that separate PCR reactions take place within each well. Generating the droplets and incorporating the relevant reagents into the droplets often comprises a large cost of the entire the system. This adds complexity and cost to the overall assay.

The present disclosure describes techniques that can be used to perform digital PCR without the use of droplet generation. A system in accordance with the presently disclosed techniques bypasses the droplet generation of digital droplet PCR by using separate, solid, distributed chambers, referred to herein as chamber particles. The chamber particles are small mobile chambers resembling hollow beads that have an internal chamber for the nucleic acid amplification process to occur. The use of chamber particles obviates the need for droplet generation and therefore simplifies the system. Additionally, the chamber particles allow for easy integration with Thermal Inkjet (TIJ) microfluidics without the complexity of a droplet generator.

Each chamber particle can be labeled to facilitate identification and analysis of the assay results. For example, the chamber particles may be labeled (e.g., barcoded) with a marker such as a set of fluorescent, absorbent, Raman, or IR markers that correspond with the primer set included in the chamber particle. This allows simultaneous analysis of a nucleic acid sample by multiple primers in a single assay.

In some examples, the chamber particles are pretreated to contain some or all of the reagents need for nucleic acid amplification to occur, such as such as primers, a polymerase enzyme, dNTPs, cofactors, amplification indicators, buffers, and the like. The reagents may be lyophilized to immobilize the reagents within the chamber particles, thus enabling the reagents to be stored within the chamber particles for later use, and simplifying the PCR process.

The digital dropletless PCR system described herein operates by obtaining a sample and extracting and purifying the nucleic acid out of it. The system then combines the purified nucleic acid aqueous solution with dry chamber particles. When the dry chamber particles encounter the aqueous solution containing the nucleic acid of interest, the solution imbibes into the chamber of the particles. Due to the dilution of the nucleic acid solution and the size of the internal volume within each chamber particle, each chamber particle will have at most a single copy of the nucleic acid of interest, and some chamber particles may have no copy. In examples in which the chamber particles are pre-treated with PCR reagents, the nucleic acid aqueous solution dissolves the reagents within the internal chamber of the chamber particle. The chamber particles are then removed from aqueous phase and moved to an oil phase to isolate each internal chamber, and the nucleic acid amplification reaction occurs within the chamber particle. After amplification, the result of the amplification and the identity of the barcode can be read, the barcode indicating the primer set (i.e., the target nucleic acid sequence) and the result of the amplification indicating whether the target nucleic acid sequence is present within the chamber particle.

Some examples of analyses that can be performed using the present techniques include the analysis of single cells, and rare cells, such as in detection and identification of sepsis, fetal cells, circulating tumor DNA, and circulating tumor cells. These analyses may assist in the functional analysis of genes, diagnosis and monitoring of hereditary diseases, amplification of ancient DNA, analysis of genetic fingerprints for DNA profiling in forensic science and parentage testing, detection of pathogens for the diagnosis of infectious diseases, and others.

FIG. 1A is a cross sectional view of an example chamber particle. The chamber particle 100 shown in FIG. 1 is in the shape of a hollow cylinder. The hollow space, i.e., the chamber 102, within the chamber particle 100 provides a volume in which to perform nucleic acid amplification. When the chamber particle 100 is contacted with a nucleic acid solution, only a single molecule of the nucleic acid of interest, at most, will enter the chamber 102. This can be controlled by diluting the nucleic acid solution to a concentration that ensures that the internal volume of the chamber particle will statistically receive, at most, one nucleic acid particle. In examples, the internal diameter 104 of the chamber may be within a range of approximately 1 to 190 micrometers, the external diameter 106 of the chamber particle may be approximately 10 to 200 micrometers, and the height 108 of the chamber particle may be approximately 0.5 to 5 times the external diameter. In some embodiments, the internal diameter 104 of the chamber may be within a range approximately 5 to 20 micrometers. Various other shapes and sizes are possible.

The walls 110 of the chamber particle 100 may be formed of any suitable material, including glasses such as silicate glasses, crystalline or polycrystalline silicon, polymer materials such as epoxy, and the like. In some examples, the walls 110 of the chamber particle 100 may be formed of SU-8 photoresist.

The chamber particle may also be magnetic. For example, the chamber particle can be magnetized by adding a magnetic material such as iron oxide particles to the material that forms the chamber walls. As used herein, the term magnetic refers to materials or objects that are affected by magnetic fields. The term magnetic does not necessarily imply that permanent or semi-permanent magnetic fields are formed by an object described as magnetic. While a magnetic item may include items that produce magnetic fields, the use of the phrase "magnetic" in this disclosure also includes objects that can be attracted to magnets or items to which magnets are attracted. The term "magnetized" refers to objects that produce permanent or semi-permanent magnetic fields including permanent magnets and induced magnets. Causing the chamber particles to be magnetic enables the use of magnets to hold, move, or otherwise manipulate the chamber particles within a system for performing PCR.

In some examples, the chamber particle 100 includes a reagent mixture 112 that includes one or more reagents for performing a nucleic acid amplification and analysis. The reagent mixture may include a mixture referred to herein as a master mix. A master mix, as that term is used herein, refers to all of the reagents needed for the nucleic acid amplification and analysis except for the primers. For example, the master mix can include an amplification enzyme (e.g., DNA polymerase), deoxynucleotide triphosphates (dNTPs), a buffer, and a cofactor. The master mix can be combined with the primer set to form a reagent mixture customized for the detection of a specific DNA sequence identified by the primer set. In some examples, the reagent mixture added to the chamber particles 100 includes the master mix and the primers. In other examples, the chamber particles may include only the primers, and the master mix can be added during the assay. Other combinations are also possible.

The reagent mixture 112 may be a dry film deposited on the internal walls of the chamber 102. In some examples, the reagent mixture may be formed by introducing a reagent solution to the chamber 102 and lyophilizing the reagents within the chamber particle 100. Lyophilizing removes the water from the reagent mixture and immobilizes the reagents within the chamber particle 100 while also preserving the chemical integrity of the various reagents.

The reagent mixture may include some or all of the reagents used to perform a PCR amplification and nucleic acid analysis, including DNA polymerase, primers, Deoxynucleoside triphosphates (dNTPs), a buffer, and a cofactor. The dNTPs are nucleotides that serve as the building blocks of a nucleic acid, such as DNA. The DNA polymerase is an amplification enzyme that, under the right conditions, will cause a target segment of DNA to be replicated by assembling the dNTPs according to the sequence exhibited by the target segment of DNA, which serves as a template. The buffer is a chemical that, in solution, provides a suitable chemical environment for optimum activity and stability of the DNA polymerase. The cofactor is a chemical that is used to activate the enzymatic activity of the DNA polymerase.

An example of DNA polymerase that can be used includes polymerase sold under the trademark KAPA2G™ available from Kapa Biosystems, a Foreign Corporation registered in Massachusetts as a division of Roche Company headquartered in Basel, Switzerland. Another example of DNA polymerase that can be used include polymerase sold under the trademark PHUSION™ or PHIRE™ available from Thermo Fischer Scientific® Inc. headquartered in Waltham, Mass. An example of a suitable cofactor includes Magnesium chloride ($MgCl_2$).

The primers are short single-strand DNA fragments that form a complementary sequence to a target region of the DNA sample under test. In PCR, two primers specific to a particular DNA fragment to be amplified by the PCR process can be included in the reagent mixture 112. If the DNA fragment corresponding to the primers is not present in the sample under test, then amplification of the target segment will not occur. If the DNA fragment corresponding to the primer is present, amplification will occur.

Selection of the primer set will depend on the target to be identified within a sample of DNA. The identity of the primers included within a specific chamber particle indicates the genomic information included within the DNA sample in the event that amplification occurs. For example, the primers may correspond with a specific gene sequence know to be present with a certain type of virus. In this case, a positive test result indicating that amplification has occurred would indicate the presence of viral DNA within the DNA sample. In other words, since the primers are known, the genotyping information of the sample can be identified. Various primers may be used to identify specific genes within human DNA, identify a particular type of virus or bacteria, etc.

In some embodiments, the reagent mix can include one or more amplification indicators used to determine whether the targeted nucleic acid sequence is present within the chamber particle. One type of amplification indicator is a fluorescent intercalating dye whose fluorescence increases when it intercalates nucleic acid. The fluorescence can be detected by an optical system. The detection of florescence associated with a chamber particle indicates that the targeted nucleic acid sequence is present within the chamber particle.

In some examples, the walls of the chamber particle can incorporate one or more identification indicators used to identify the chamber particle's type, which indicates the primer set used in the reagent mix. The identification indicators may be referred to herein as a barcode. The barcode for a specific chamber particle can be specified to coincide with the primer set used in the reagent mix. In this way, the detection of the barcode identifies the primer set and, by extension, the nucleic acid sequence that was amplified. The barcode can be created by embedding one or more of the identification indicators within the material making up the chamber particle. Examples of suitable identification indicators include colored dies, color absorbent markers, florescent markers, Raman markers, Infrared markers, and others. The barcoding of individual chamber particles allows multiple primer sets and multiple targets to be tested for within a single assay and a single piece of PCR equipment.

Figure 1B:
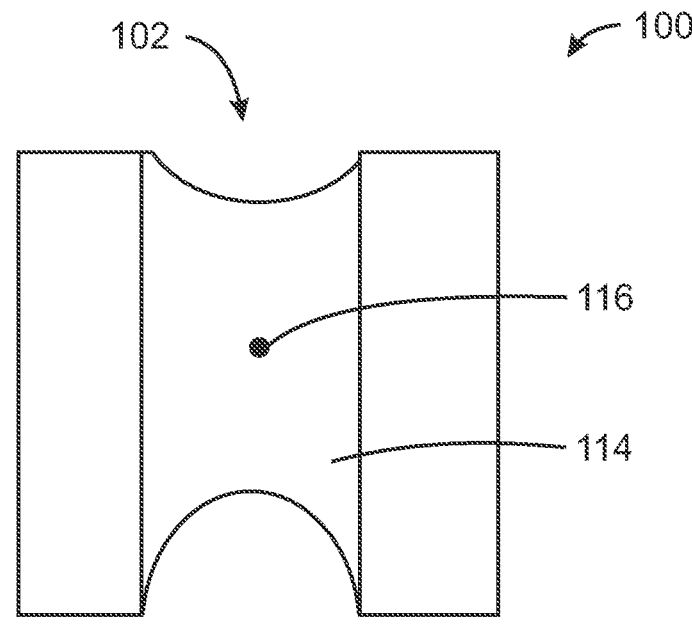
FIG. 1B shows the chamber particle of FIG. 1A after the chamber particle is contacted with the nucleic acid solution.

FIG. 1B shows the chamber particle of FIG. 1A after the chamber particle is contacted with the nucleic acid solution. The nucleic acid solution 114 is an aqueous solution that includes that nucleic acid of interest and may also include some of the reagents used to perform a PCR amplification and nucleic acid analysis, including DNA polymerase, Deoxynucleoside triphosphates (dNTPs), a buffer, cofactor, and others. Any reagents needed for the nucleic acid amplification and analysis that are not included in the pre-treated chamber particle may be included in the nucleic acid solution instead. The surface of the chamber particle 100 is hydrophilic. Therefore, contact with the nucleic acid solution 114 will cause the nucleic acid solution to imbibe into the internal chamber 102. The nucleic acid solution 114 will be diluted to be statistically ensured by Poisson distribution that only one nucleic acid particle, at most, will be included within the internal chamber 102.

After the nucleic acid solution 114 is imbibed within the chamber 102 of the chamber particle 100, the aqueous solution will begin to dissolve the lyophilized reagents 112 included within the pre-treated chamber particle 100. After a sufficient time has passed for all of the reagents to dissolve, the amplification process can be initiated.

Figure 2A:
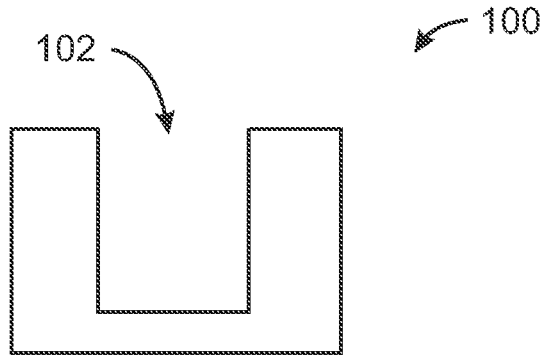
FIGS. 2A-2C is a cross sectional views of additional chamber particles in accordance with examples.
Figure 2B:
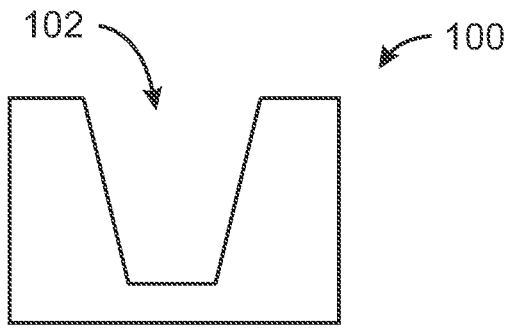
Figure 2C:
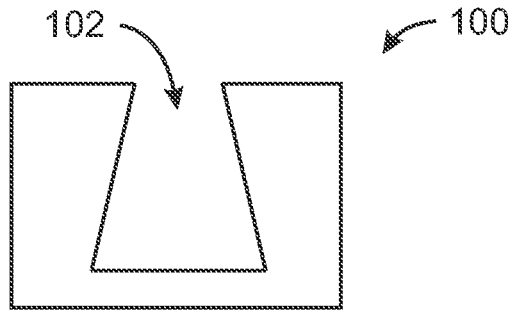

FIGS. 2A-2C is a cross sectional views of additional chamber particles in accordance with examples. The chamber particles 100 shown in FIGS. 2A-2C are similar to the chamber particle of FIG. 1, except that the chamber particles 100 are shaped like a cup. Unlike the chamber particle of FIG. 1, which has a through hole, the chamber particles of FIG. 2A-2C have a bottom surface and the chamber 102 is open only at one end. The bottom surface of the chamber 102 may help the chamber particle to better retain the nucleic acid solution and other reagents.

In FIG. 2A, the internals walls of the chamber 102 are substantially straight. By contrast, the chamber particle of FIG. 2B is tapered outward from the bottom of the chamber 102 toward the top of chamber 102. The outward taper may assist the penetration of the nucleic acid solution into the chamber 102.

In FIG. 2C the chamber particle is tapered inward from the bottom of the chamber 102 toward the top of chamber 102. The inward taper may be useful to further help the chamber particle 100 to retain the nucleic acid solution and other reagents.

The chamber particles 100 shown in FIGS. 2A-2C may be used in same manner described above in relation to FIGS. 1A and 1B. For example, the chamber particles 100 may be pre-treated with some or all of the reagents used in the amplification process. Furthermore, it will be appreciated that additional shapes may also be possible.

Figure 3:
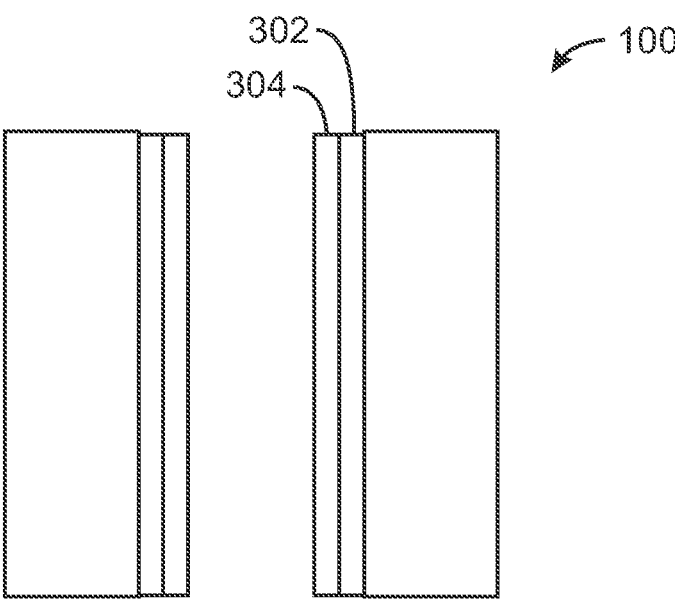
FIG. 3 is a cross sectional view of another chamber particle in accordance with examples.

FIG. 3 is a cross sectional view of another chamber particle in accordance with examples. The chamber particle 100 shown in FIG. 3 is similar to the chamber particle of FIG. 1, except that the reagents are added to the chamber particle 100 in separate layers. The chamber particle 100 of FIG. 3 includes two layers of reagents, the primer layer 302 and the additional reagent layer 304. The primer layer 302 includes the primers, which may be attached to the surface, often with a covalent bond. The additional reagent layer may be a master mix and can include one or more of the additional reagents used for the amplification and analysis process, including the DNA polymerase, dNTPs, a buffer, and a cofactor, for example.

The layers may be formed by successive depositions. For example, the primer layer 302 can be formed by introducing a primer solution into the chamber, lyophilizing the primer solution, and then introducing the additional reagents to be added to the additional reagent layer 304 and lyophilizing the additional reagents. Forming different reagent layers in successive iterations may be useful to make the manufacturing of pre-treated chamber particles more efficient. For example, separate groups of chamber particles may undergo separate deposition processes for the primer layer 302 so that each group can receive a different primer set. After customizing each group of chamber particles, all of the chamber particles may be treated together for the addition of the additional reagent layer 304.

The layers may be created in a different order compared to what is shown in FIG. 3. Additionally, the layered configuration shown in FIG. 3 is applicable to additional chamber particle shapes, including the chamber particle shapes shown in FIGS. 2A-2C.

Figure 4:
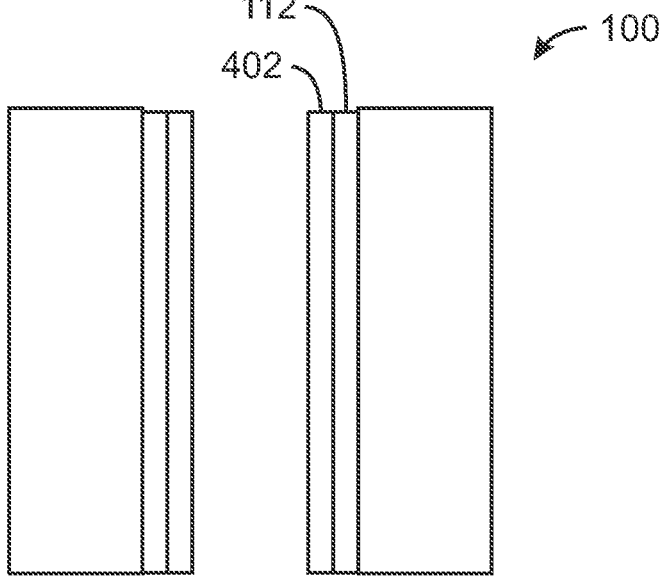
FIG. 4 is a cross sectional view of another chamber particle in accordance with examples.

FIG. 4 is a cross sectional view of another chamber particle in accordance with examples. The chamber particle 100 shown in FIG. 3 is similar to the chamber particle of FIG. 1, except that the chamber particle 100 includes a delayed delivery film 400. As in FIG. 1, the chamber particle 100 includes the reagent mixture 112, which may include some or all of the reagents used for the amplification and analysis process, including the DNA polymerase, primers, Deoxynucleoside triphosphates (dNTPs), a buffer, and a cofactor, for example. The reagent mixture may be formed by introducing a reagent solution to the chamber 102 and lyophilizing the reagents within the chamber particle 100.

After the reagent mixture is lyophilized, the delayed delivery film 400 may be deposited over the lyophilized reagent mixture 112. Suitable films include sucrose, dextrose, trehalose, or a mixture thereof. Other water soluble materials may also be used. The film may be formed by introducing a solution containing the film material to the chamber 102 and lyophilizing the solution within the chamber particle 100 to form a film that covers the lyophilized reagent mixture 112.

The delayed delivery film 400 delays the solvation of the lyophilized reagent mixture into solution. This can help to ensure that the reagents dissolve in the oil phase at which point the reagent solution will be trapped within the chamber particle. In this way, the risk of cross talk between chamber particles with different primer sets can be reduced. The delayed delivery film 400 shown in FIG. 4 may also be applied to the multi-layer reagent configuration described in relation to FIG. 3 and other chamber particle shapes, including the chamber particle shapes shown in FIGS. 2A-2C.

Figure 5:
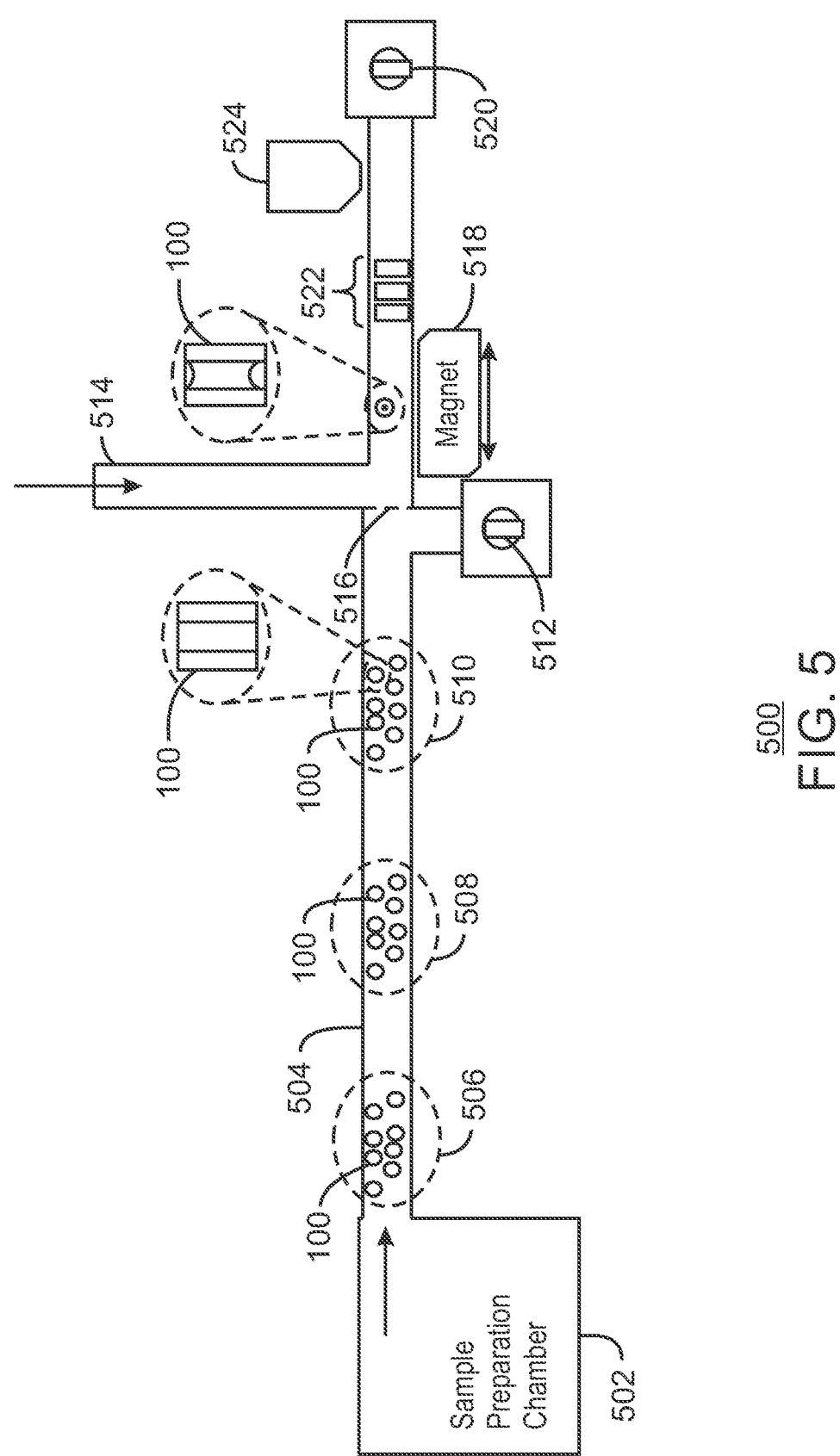
FIG. 5 is a diagram of a microfluidic device for performing PCR, in accordance with examples.

FIG. 5 is a diagram of a microfluidic device for performing PCR, in accordance with examples. It will be appreciated that the diagram is a simplified representation of a microfluidic device 500, and that the microfluidic device in accordance with examples can have additional elements not shown in FIG. 5. In some examples, the microfluidic device

500 is disposed on a chip, which can be loaded into an instrument for performing PCR or other nucleic acid amplification tests.

The microfluidic device 500 can include a sample preparation chamber 502. The sample preparation chamber 502 can be a reservoir in which the nucleic acid solution is prepared. For example, after insertion of a sample (e.g., blood) into the sample preparation chamber 502, the sample can then be pre-concentrated, any cells containing the sample can be lysed, and the nucleic acids may be absorbed, washed and eluted. The sample can then be diluted to a specified concentration suitable for digital PCR. In some examples, the sample preparation chamber 502 can be eliminated and sample preparation can be performed separately. The nucleic acid solution contains the nucleic acid of interest and, depending on the details of a specific implementation, may also include some of the reagents needed for amplification and analysis.

The nucleic acid solution can then be introduced to a microfluidic channel 504, which contains a plurality of chamber particles 100. Prior to introduction of the nucleic acid solution, the chamber particles 100 will be in the form of a dry powder. The chamber particles 100 may be any of the chamber particles described above in relation to FIGS. 1-4.

In the example shown in FIG. 5, the microfluidic channel 504 is loaded with three different types of chamber particles 100, which are shown as group A 506, group B 508 and group C 510. Each group of chamber particles 100 may differ with respect to the primer set included within the chamber particle. This allows for different nucleic acid sequences to be tested for within a single assay.

The nucleic acid solution can be pulled through the microfluidic channel 504 by a pull pump 512. As the nucleic acid solution flows through the channel 504, it encounters the chamber particles 100 and the chamber particles 100 become entrained within the solution flow. The nucleic acid solution imbibes within the chamber particles 100 and begins to dissolve the reagents and/or the delayed delivery film, depending on the specific configuration of the chamber particle 100.

The chamber particles 100 are pulled toward an oil-phase microfluidic channel 514. The oil-phase microfluidic channel 514 may be separated from the aqueous-phase microfluidic channel 504 by a porous semipermeable membrane 516. When the chamber particles 100 reach interface between the aqueous-phase microfluidic channel 504 and the oil-phase microfluidic channel 514, the chamber particles 100 will move into the oil-phase microfluidic channel 514. For example, in examples wherein the chamber particles 100 are magnetic, the chamber particles 100 can be pulled into the oil phase by a magnet, which may be a permanent magnet or a coil such as a Helmholtz coil configured to generate a magnetic field. Once in the oil-phase, the oil surrounding the chamber particles 100 will confine the nucleic acid solution and reagents within each chamber particle 100, preventing cross talk between chamber particles 100.

The oil-phase microfluidic channel 514 is also coupled to another pull pump 520 which pulls the chamber particles 100 through the oil-phase microfluidic channel 514 to an amplification region 522 and then a detection region 524. The amplification region 522 is a region of the chip in which nucleic acid amplification is induced by the instrument in which the chip is inserted. The instrument can induce the amplification through any suitable means, including isothermal amplification such as Loop-mediated isothermal amplification (LAMP), or thermocylcing, for example. Accordingly, the instrument may include a heating element to control the temperature of the chamber particles within the amplification region. Depending on the particular technique used, the temperature may be held at a constant temperature or the temperature may be cycled through a series of alternating temperature steps. Repeated thermocycling aids in denaturing the DNA and allowing the primers to potentially bind to a target such that replication of the target can occur as the amplification region 522. In an example, a thermocycling element can include a heater, thermoelectric cooler (TEC), air cooling, liquid cooling or other components that may controllably raise or lower the temperature in the amplification region.

After the amplification process is completed, the chamber particles 100 can be moved from the amplification region 522 to the detection region 524 to detect the results. Accordingly, the instrument may include an optical system, such as a florescence microscope, for detecting the amplification indicators for each chamber particle separately. For example, the optical system can detect the presence of fluorescence created by intercalating dyes. The optical system can also read the barcode applied to the chamber particles 100 by detecting the identification indicators added to the chamber particle material. The chamber particles 100 can be moved through the detection region 524 and analyzed one at a time. The results may be read by the instrument and stored electronically for further processing or to be displayed to the user.

Figure 6:
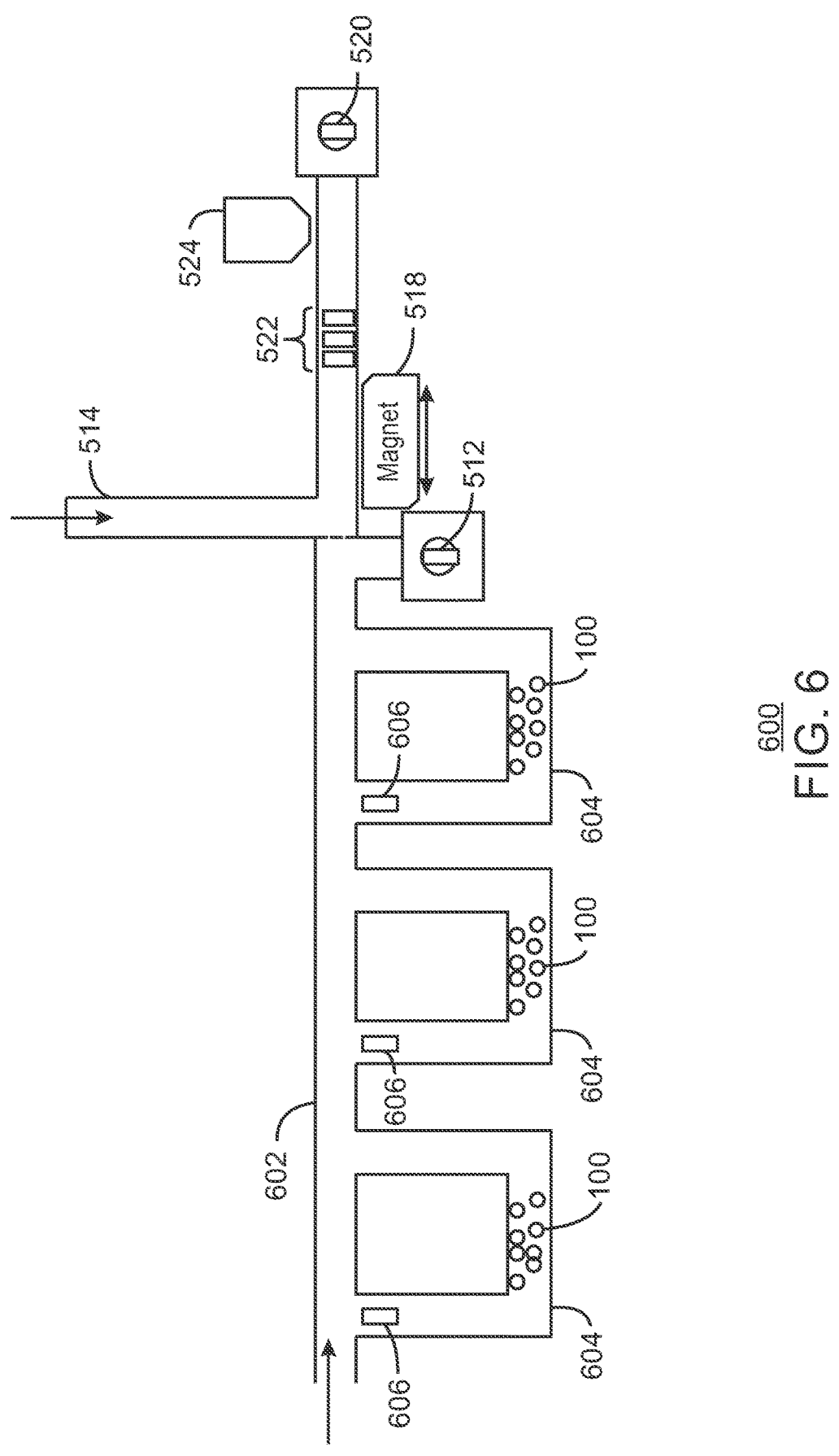
FIG. 6 is a diagram of another example microfluidic device for performing PCR, in accordance with examples.

FIG. 6 is a diagram of another example microfluidic device for performing PCR, in accordance with examples. The microfluidic device 600 of FIG. 6 is similar to the microfluidic device 500 of FIG. 5 and operates in a similar manner. In the microfluidic device 600 of FIG. 6, the aqueous-phase microfluidic channel includes a main channel 602 and a number of branches 604 for controlling the type of nucleic acid analysis to be performed. Although three branches are shown, it will be appreciated that the device can include any suitable number of branches, including 2, 4, 5, 6 or more. Each branch 604 is loaded with a different type of chamber particle, e.g., chamber particles with a different primer set. Each branch 604 may be coupled to a push pump 606 which determines whether the corresponding branch is activated. If a branch is activated, the nucleic acid solution with flow through the branch and entrain the chamber particles contained therein. Any combination of the available branches may be activated. In this way, the user can specify which of the available primer sets will be used in a specific assay. The remaining elements of the testing process may be the same as those described in relation to FIG. 5.

Figure 7:
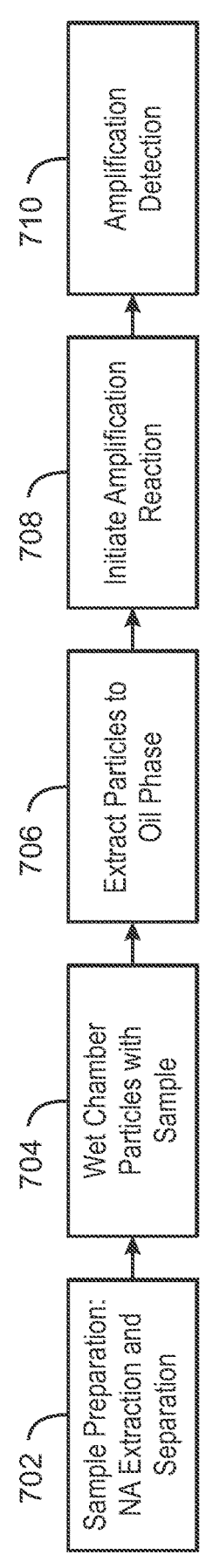
FIG. 7 is a process flow diagram summarizing a method of performing nucleic acid amplification process in accordance with examples.

FIG. 7 is a process flow diagram summarizing a method of performing nucleic acid amplification process in accordance with examples. The method 700 may be performed by an electronic instrument configured to perform digital PCR and other types of amplification processes using the microfluidic device 500 or 600 described above. However, some or all of the actions shown in FIG. 7 may be performed manually using suitable lab equipment or separate instrumentation.

At block 702, the nucleic acid sample of interest is prepared. For example, the nucleic acid can be extracted and separated from other components of the biological sample (e.g., blood). The nucleic acid sample can then be diluted to the desired concentration. In some examples, preparing the nucleic acid sample includes adding a set of primers and a master mix that includes reagents such as DNA polymerase, dNTPs, a buffer, and cofactor, for example. In some examples, the primers and/or the master mix is included in the chamber particles and is therefore not added to the nucleic acid sample. Additionally, some components of the reagent mixture may be added to the nucleic acid sample, while other components may be included within the chamber particles as a pre-treatment. The result of the sample preparation performed at block 702 is a purified nucleic acid aqueous solution, optionally containing one or more reagents.

At block 704, dry chamber particles are wetted with the nucleic acid solution. The chamber particles may be any of the chamber particles described herein and may be pre-treated to include a set of primers and other reagents. After the chamber particles are wetted, each chamber particle will include, at most, one copy of the nucleic acid. This can be controlled by controlling the concentration of nucleic acid within the sample with respect the size of the internal chamber within the chamber particle. At this point, the chamber particle will also include all of the reagents used to perform amplification and analysis of the results.

At block 706, the chamber particles are extracted to an oil phase. In the oil-phase, each chamber particle is immersed in an oil that isolates each internal chamber.

At block 708, the amplification reaction is induced. The amplification reaction can be induced using an isothermal amplification process, for example a LAMP process. After the amplification process is complete, the process flow can advance to block 710.

At block 710, the result of the amplification can be detected and the barcode can be read to identify the chamber particle type. The barcode indicates the primer set (i.e., the target nucleic acid sequence) and the result of the amplification indicates whether the target nucleic acid sequence is present within the chamber particle.

It is to be understood that the block diagram of FIG. 7 is not intended to indicate that the method 700 is to include all of the actions shown in FIG. 7. Rather, the method 700 can include fewer or additional components not illustrated in FIG. 7.

FIGS. 8A through 8F illustrate an example technique for fabricating chamber particles. The chamber particles may be fabricated using any suitable semiconductor fabrication techniques. For example, the creation of various structures may be accomplished though deposition, removal, and patterning of structures. Deposition techniques include techniques such as chemical vapor deposition, electrochemical deposition, spin coating, and others. The patterning of various features maybe accomplished through the use of photolithography in combination with various etching techniques, including wet etching techniques and plasma etching techniques, for example.

Figure 8A:
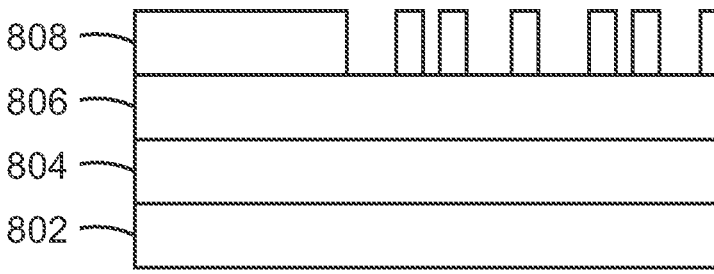
FIGS. 8A through 8F illustrate an example technique for fabricating chamber particles.
Figure 8B:
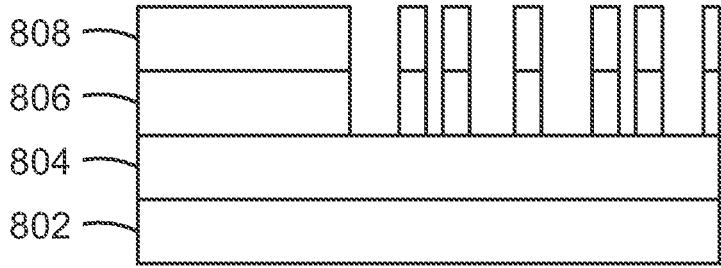
Figure 8C:
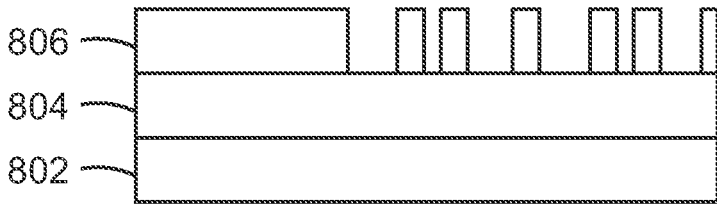
Figure 8D:
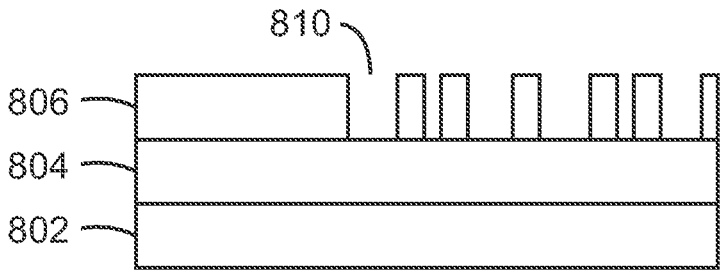

FIG. 8A shows a structure that includes a substrate layer 802, a release layer 804, a chamber particle layer 806, and a mask layer 808. The substrate layer 802 may be any suitable substrate, including glass, polymers, silicon, and the like. The release layer 804 is formed over the substrate and can include a thermal release layer or ultraviolet (UV) release layer, for example. The release layer 804 may be an adhesive film that can be rolled over the substrate layer 802.

The chamber particle layer 806 is formed over the release layer 804. The chamber particle material may be any suitable material, including polymers such as SU8. The chamber particle layer 806 can be formed by spin-coating a polymer over the release layer 804, for example. The chamber particle layer 806 may also be infused with magnetic particles and one or more identification indicators used to form a barcode that identifies the chamber particle type (e.g., primer set). The magnetic particles and one or more identification indicators can be mixed into the polymer before spin-coating the polymer on top of the release layer 804.

The mask layer 808 may then be deposited over the chamber particle layer 806 and patterned to form the outline of a plurality of chamber particles. The mask layer 808 may be a photolithography mask such as SU8, Polydimethylsiloxane (PDMS), polymethylmethacrylate, phenol-formaldehyde resin and any other positive or negative photoresist. The patterning process can be performed using photolithography, embossing, silk screening, or any other suitable micro-patterning technique.

Next, as shown in block 8B, the chamber particle layer 806 is etched to form the walls of the chamber particles. The chamber particle layer 806 may be etched using Reactive-Ion Etching (RIE), which is a type of dry etching that uses chemically reactive plasma to remove material deposited on wafers. The mask protects the material underneath it, leaving the walls of the chamber particles intact.

Next, as shown in block 8C, the mask can be removed. The mask may be removed by any suitable solvent and depends on the type of material used for the mask.

Next, as shown in block 8D, a reagent mixture 810 is deposited over the chamber particle layer 806. The reagent mixture can include the master mix, the desired primer set, or some combination thereof depending on the implementation details of a specific example. The reagent mixture 810 is an aqueous mixture that penetrates into the spaces formed in the chamber particle layer 806 by the etching process.

Figure 8E:
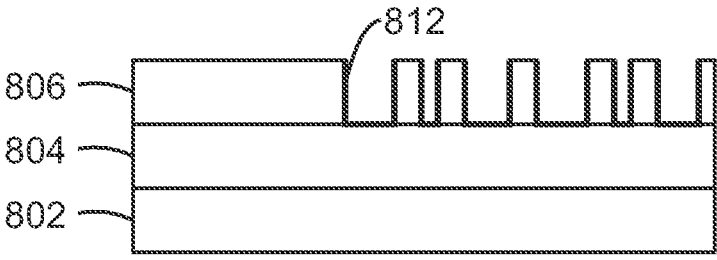

Next, as shown in FIG. 8E, the reagent mixture is lyophilized. This causes the reagent mixture to dry, forming a dry film 812 that adheres to the walls of the chamber particles. Additional layers, such as different layers of reagents or a delayed delivery film, may be formed by successive deposition and lyophilization of additional materials.

Figure 8F:
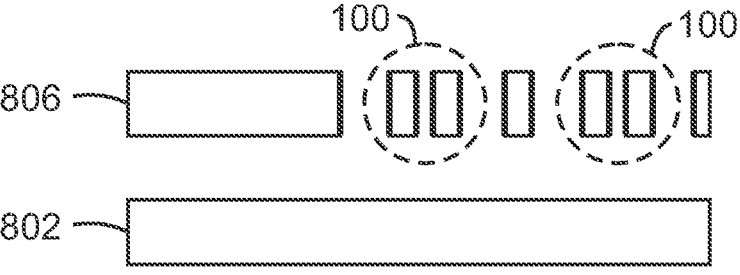

Next, as shown in FIG. 8F, the release layer 804 can be removed, for example, by heating or radiating with UV radiation, thereby releasing the individual chamber particles 100.

Figure 9A:
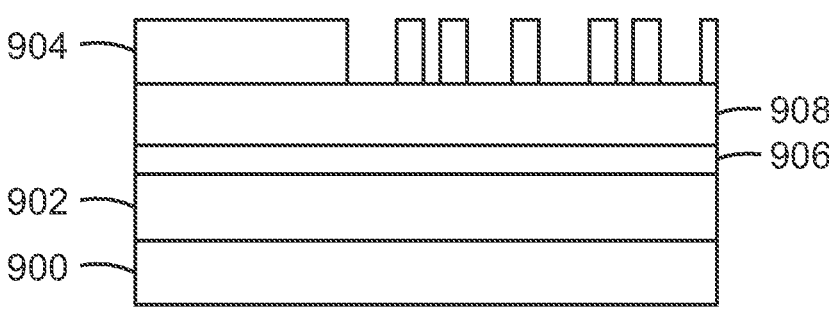
FIGS. 9A through 9F illustrate another example technique for fabricating chamber particles.
Figure 9B:
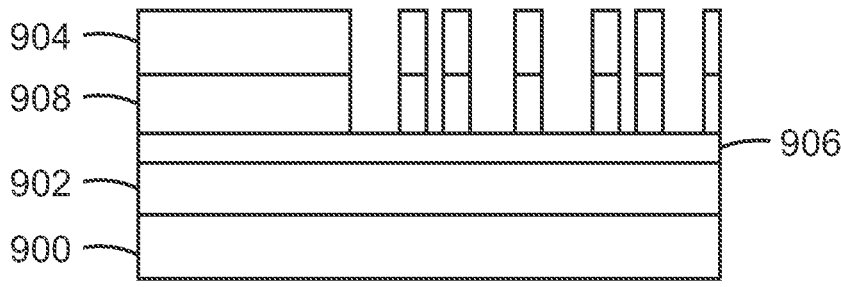
Figure 9C:
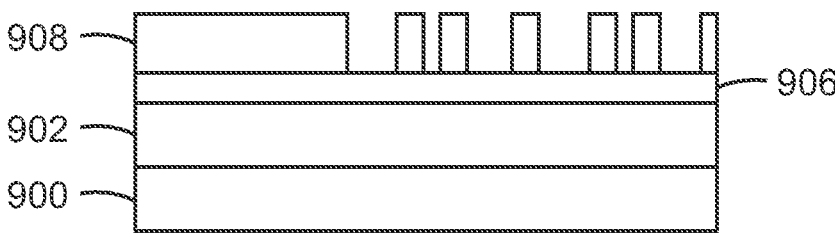
Figure 9D:
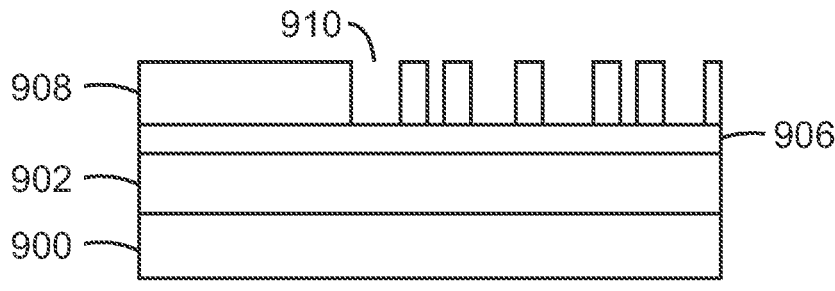

FIGS. 9A through 9F illustrate another example technique for fabricating chamber particles. FIG. 9A shows a structure that is similar to that of FIG. 8A, in that it includes a substrate layer 900, a release layer 902, and a mask layer 904. However, the structure shown in FIG. 9A includes two layers of chamber particle material, referred to herein as a base layer 906 and a side wall layer 908.

The substrate layer 900 and release layer 902 may be formed as described in relation to FIG. 8A. The base layer 906 is then formed over the release layer 902, and the side wall layer 908 is formed over the base layer 906. The chamber particle material used for the base layer 906 and side wall layer 908 may be the same material, and may include polymers such as SU8. However, in some examples, the material used for the base layer 906 and side wall layer 908 may be different. For example, the base layer material may be silicon, and the side wall material silicon dioxide (SiO2). Before applying the mask layer 904, the chamber particle material may be infused with magnetic particles and one or more identification indicators used to form a barcode that identifies the chamber particle type (e.g., primer set). The mask layer 904 may then be deposited over the side wall layer 908 and patterned to form the outline of a plurality of chamber particles.

Next, as shown in block 9B, the side wall layer 908 is etched to form the walls of the chamber particles using reactive-ion etching, for example. The etching process penetrates through the side wall material 908 while leaving the base material intact 906. The depth of the etch may be controlled by controlling the etching time in accordance with a known etch rate.

Next, as shown in block 9C, the mask is removed.

Next, as shown in block 9D, a reagent mixture 910 is deposited over the side wall layer 908, filling the spaces (e.g., cups) formed by the etching of the side wall layer 908. The reagent mixture 910 can include the master mix, the desired primer set, or some combination thereof depending on the implementation details of a specific example.

Figure 9E:
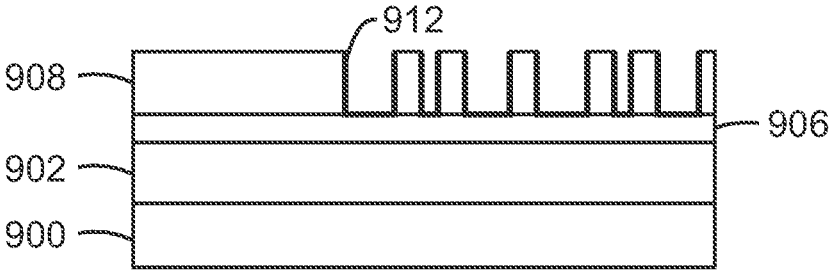

Next, as shown in FIG. 9E, the reagent mixture is lyophilized, causing the reagent mixture to dry and form a film 912 that adheres to the internal surfaces of the chamber particles. Additional layers, such as different layers of reagents or a delayed delivery film, may be formed by successive deposition and lyophilization of additional materials.

Figure 9F:
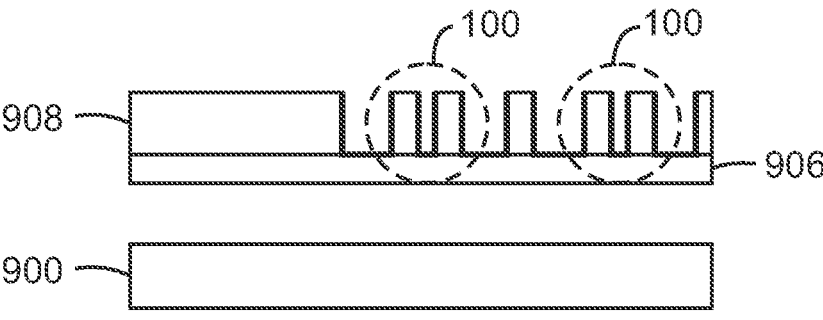

Next, as shown in FIG. 9F, the release layer can be removed by heating or UV radiation, thereby releasing the base layer 906 and side wall layer 908 forming the chamber particles 100. At this point, the chamber particles 100 will be coupled together via the base layer 906. The chamber particles 100 can be separated from one another using laser singulation.

FIGS. 10A through 10D illustrate another example technique for fabricating chamber particles. FIG. 10A shows a capillary fiber 1000, which serves as the chamber particle material for forming a plurality of chamber particles. The capillary fiber 1000 may be glass or polymer, for example. In some examples, the capillary fiber 1000 can include magnetic particles and one or more identification indicators used to form a barcode that identifies the chamber particle type (e.g., primer set).

As shown in block 10B, a reagent mixture 1002 is loaded into the capillary fiber 1000 and fills the volume inside the capillary fiber 1000. The reagent mixture 1002 can include the master mix, the desired primer set, or some combination thereof depending on the implementation details of a specific example.

Next, as shown in FIG. 10C, the reagent mixture is lyophilized. This causes the reagent mixture to dry and form a film 1004 that adhere to the walls of the capillary fiber 1000. After lyophilizing the reagent mixture, additional layers may be deposited inside the capillary fiber. For example, a delayed delivery film may be deposited over the lyophilized reagent mixture using chemical vapor deposition. The delayed delivery film may be a polyactide formed by depositing a monomer over the surface of the lyophilized reagent mixture via chemical vapor deposition and polymerizing the monomer on the surface.

A delayed delivery film may also be formed by aerosol layering. Aerosol layering may be accomplished by aerosolizing a concentrated solution of the film material (e.g., trehalose), depositing the aerosol on the surface of the lyophilized reagent mixture, and allowing it to dry. Successive iterations of aerosol deposition and drying may be repeated until a desired level of the film thickness is achieved.

Next, as shown in FIG. 10D, the capillary fiber 1000 can be laser cut along its cross-section to form the individual chamber particles 100.

While the present techniques may be susceptible to various modifications and alternative forms, the techniques discussed above have been shown by way of example. It is to be understood that the technique is not intended to be limited to the particular examples disclosed herein. Indeed, the present techniques include all alternatives, modifications, and equivalents falling within the scope of the following claims.

What is claimed is:

1. A method of performing a nucleic acid amplification reaction, comprising:

generating a nucleic acid solution comprising a plurality of nucleic acid molecules;

combining the nucleic acid solution with a plurality of chamber particles, each chamber particle comprising:

a chamber for receiving the nucleic acid solution, wherein the chamber comprises a hollow space surrounded by walls forming a single opening of the chamber, and wherein the chamber receives, at most, one of the plurality of nucleic acid molecules through the single opening into the hollow space; and reagents for causing a polymerase chain reaction within the chamber, wherein the chamber particle comprises a magnetic material;

moving the chamber particles from an aqueous phase to an oil phase via a magnetic field;

inducing the nucleic acid amplification reaction to generate an amplified nucleic acid while the chamber particles are in the oil phase; and performing a detection process to detect the presence of the amplified nucleic acid within the chamber.

2. The method of claim 1, wherein the reagents comprise a dry mixture of a master mix and primers, wherein the dry mixture adheres to internal surfaces of the chamber.

3. The method of claim 1, wherein the chamber particle comprises a delayed delivery film disposed over the reagents.

4. The method of claim 1, wherein the nucleic acid amplification reaction is a digital Polymerase Chain Reaction (PCR).

\* \* \* \* \*